(12) United States Patent
Helgason et al.

(10) Patent No.: US 8,233,667 B2
(45) Date of Patent: Jul. 31, 2012

(54) APPARATUS AND METHOD FOR ANALYSIS OF SIZE, FORM AND ANGULARITY AND FOR COMPOSITIONAL ANALYSIS OF MINERAL AND ROCK PARTICLES

(75) Inventors: Thorgeir Helgason, Reykjavik (IS); Jason Lee, Bristol (GB); Melvyn L. Smith, Bristol (GB); Agnar Thomas Moeller, Reykjavik (IS); Tryggvi Thorgeirsson, Reykjavik (IS); Vera Hofer, Klagenfurt (AT); Juergen Pilz, Klagenfurt (AT); Jon Atli Benediktsson, Reykjavik (IS)

(73) Assignee: Petro-Model EHF (IS)

( * ) Notice: Subject to any disclaimer, the term of this patent is extended or adjusted under 35 U.S.C. 154(b) by 1149 days.

(21) Appl. No.: 11/572,781

(22) PCT Filed: Sep. 7, 2005

(86) PCT No.: PCT/IS2005/000020
§ 371 (c)(1), (2), (4) Date: Dec. 17, 2007

(87) PCT Pub. No.: WO2006/027802
PCT Pub. Date: Mar. 16, 2006

(65) Prior Publication Data
US 2008/0192987 A1      Aug. 14, 2008

(30) Foreign Application Priority Data

Sep. 7, 2004   (IS) ............................................. 7440

(51) Int. Cl.
*G06K 9/00* (2006.01)
(52) U.S. Cl. ...................................................... 382/109
(58) Field of Classification Search .................. None
See application file for complete search history.

(56) References Cited

U.S. PATENT DOCUMENTS
2,778,478 A * 1/1957 Brook ........................... 198/443
(Continued)

FOREIGN PATENT DOCUMENTS
GB           2052736 A      1/1981
(Continued)

OTHER PUBLICATIONS

Smith et al., "Quantitative determination of mineral types and abundances from reflectance spectra using principal components analysis", Lunar and Planetary Institute, NASA, American Geophysical Union, et al., Lunar and Planetary Science Conference, 15th, Houston, TX, Mar. 12-16, 1984) Journal of Geophysical Research, Supplement (ISSN 0148-0227), v.*

(Continued)

*Primary Examiner* — Brian P Werner
*Assistant Examiner* — Tahmina Ansari
(74) *Attorney, Agent, or Firm* — McKee, Voorhees & Sease, P.L.C.

(57) ABSTRACT

Equipment and process for three-dimensional measurement of size and shape and for compositional analysis of mineral and rock particles and the like objects. A mixture of particles or objects of same or different sizes of minerals or rocks or the like are fed individually and automatically onto a conveyor belt for three-dimensional machine vision measurements using laser and two cameras and subsequently for spectroscopic measurements using visible and infrared light and are then collected at the end of the conveyor. Computer software is used to perform the measurement automatically and to calculate size, form, roundness, and preferably petrographic composition and other characteristics or properties of each individual object and the statistical distribution of relevant properties, either according to built-in measurement processes or user specific methods.

34 Claims, 10 Drawing Sheets

U.S. PATENT DOCUMENTS

| | | | | |
|---|---|---|---|---|
| 5,184,733 | A * | 2/1993 | Arnarson et al. | 209/585 |
| 5,309,215 | A | 5/1994 | Schumann | |
| 6,140,643 | A * | 10/2000 | Brown et al. | 850/10 |
| 6,356,646 | B1 * | 3/2002 | Spencer | 382/103 |
| 6,380,503 | B1 * | 4/2002 | Mills et al. | 209/586 |
| 6,614,928 | B1 | 9/2003 | Chung et al. | |
| 7,274,810 | B2 * | 9/2007 | Reeves et al. | 382/128 |
| 2008/0192987 | A1 * | 8/2008 | Helgason et al. | 382/109 |
| 2009/0314086 | A1 * | 12/2009 | Djordjevic | 73/579 |

FOREIGN PATENT DOCUMENTS

| | | |
|---|---|---|
| JP | 10048143 A | 2/1998 |
| WO | 03/065017 A2 | 8/2003 |

OTHER PUBLICATIONS

Mohrig D., "Sedimentary Geology", Fall 2004. MIT Course Num: 12.110, Lecture 2 "Sediment Production", p. 4 section VII "Rounding" Printed Courtesy of SEPM with permission after Powers, M.C.,1953, Journal of Sedimentary Petrology, v.23, p. 118. http://ocw.mit.edu/courses/earth-atmospheric-and-planetary-sciences/12-110-sedimentary-geology-fall-2004/.*

PCT International Search Report for PCT/IS2005/000020.

* cited by examiner

APPARATUS AND METHOD FOR ANALYSIS OF SIZE, FORM AND ANGULARITY AND FOR COMPOSITIONAL ANALYSIS OF MINERAL AND ROCK PARTICLES

FIELD OF INVENTION

The invention relates generally to equipment and methods for analysis of mineral and rock particles and specifically a novel apparatus and methods for automatic analysis of such particles based on optical and spectrophotometric methods for determining size and shape, including form and angularity, and composition of mineral and rock particles and classifying particles according to size, shape and petrographic type.

TECHNICAL BACKGROUND

Classical, manual and mechanical methods of size analysis, petrological description and other analysis of rock and mineral particles are well-established and routinely used by the construction aggregates industries for quality control and for assessment of e.g. road aggregates and concrete aggregates. However, the traditional methods often require highly trained specialists and yet it is difficult to obtain reproducible results and they are tedious, time consuming and expensive.

Methods and equipment have been described in the prior art for optical analysis of mineral and rock particles, e.g. in WO 02/090942-A1; DE 29800809-U1; DE 20117494-U1; DE 20219141-U1; U.S. Pat. No. 6,061,130; and U.S. Pat. No. 5,309,215. However, none of the methods or equipment disclosed in said documents provide a three-dimensional analysis for automatic size and shape determination (e.g. classification according to form and angularity) of mineral and rock particles, nor do they provide analysis of petrographic composition.

There is a need for methods and equipment that can provide reliable and reproducible high-throughput measurement of mineral and rock particles for determining size, shape and preferably also the composition of such particles.

SUMMARY OF THE INVENTION

It is an objective of the present invention to provide an apparatus and method for high-throughput analysis of objects/particles in a sample selected from minerals, rocks, gravel, natural, manufactured or recycled aggregates and the like for determining automatically size and shape of each particle/object in a sample comprising a plurality of particles/objects where the shape determination includes parameters defining form and angularity.

The apparatus of the present invention combines a suitable feeding system for feeding said objects in a single layer stream of certain pre-determined maximum width such that the objects are interspaced (that is not overlapping or in direct contact) with an optical image detection system configured to obtain three-dimensional surface data for each object and a control system being provided with processing means and dedicated software for processing images of said objects and to automatically determine the size, and shape of said objects and returning parameters representing the size and shape of the objects. Preferably the apparatus additionally comprises a spectroscopic detection system for obtaining spectra of the samples, which are processed by the control system to obtain data representing the composition and/or petrographic type of sample objects. The apparatus and method of the invention are able to automatically and rapidly analyze petrological samples, e.g. to assess quality and suitability for constructions, concrete, roadwork and related applications. Such analyses have hitherto been based on tedious semi-mechanical methods (sieving and grinding) and manual visual inspection.

Another aspect of the invention provides a method for determining size and shape of objects in a plurality of objects in a sample selected from minerals, rocks, gravel, natural, manufactured or recycled aggregates and the like, where the shape determination includes at least the determination of a form parameter or class indicating whether particles are elongated and/or flat and a and an angularity determination, A further aspect provides a computer program product for carrying out the data analysis and determinations in the methods described herein and controlling data acquistions.

DETAILED DESCRIPTION

The apparatus of the present invention can be configured for particular sample types but is generally suitable for automatic analysis of batch samples comprising a plurality of objects/particles such as minerals, rocks, gravel, natural, manufactured or recycled aggregates and the like.

Figure 9A:
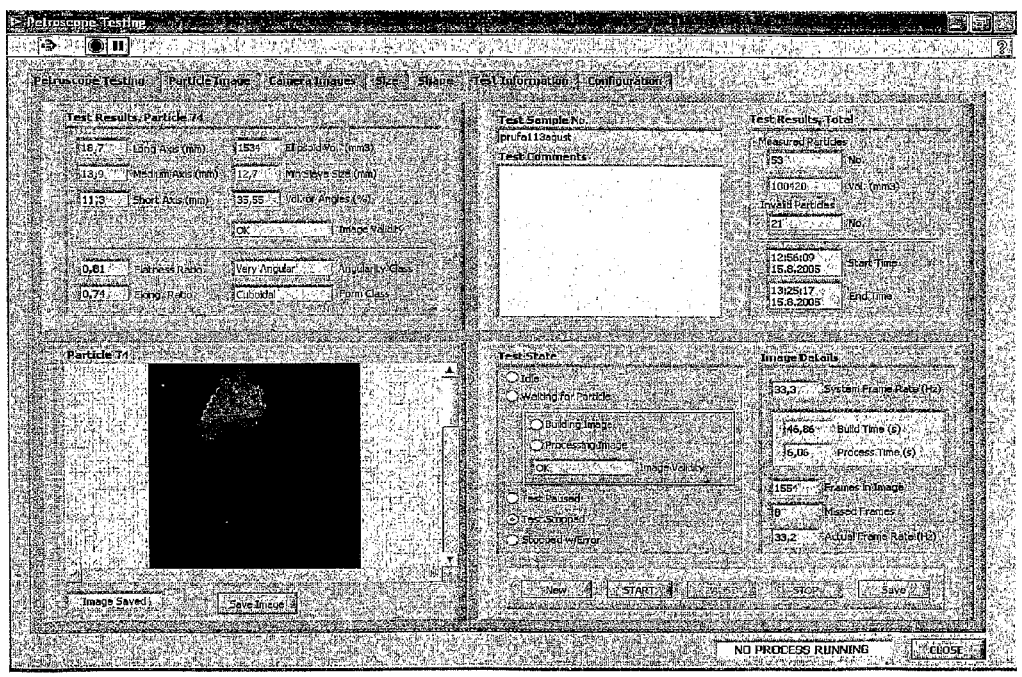
FIG. 9 shows screen views generated by computer software for implementing the invention; 9a is a view showing measurement data for a single object, including length of axes, angularity class, form class form, volume of angles and more; 9b shows accumulated particle size distribution for a sample, both based on sample volume (left) and sample object number (right); 9c shows the distribution of sample objects in angularity and form classes, both based on volume (left) and number (right)
Figure 9B:
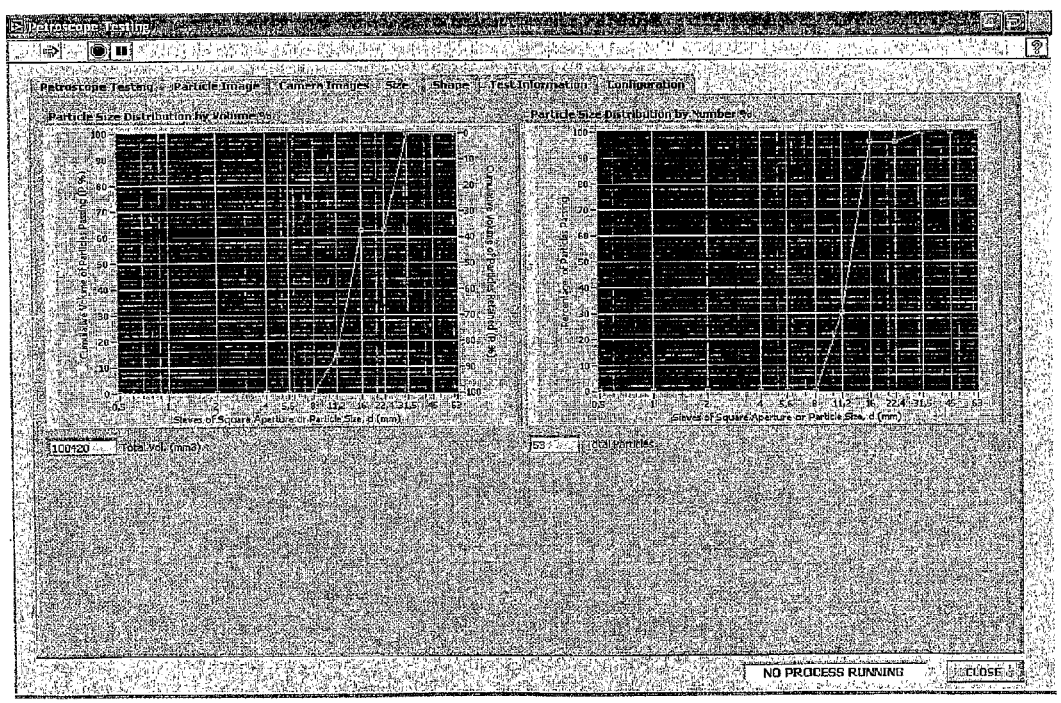
Figure 9C:
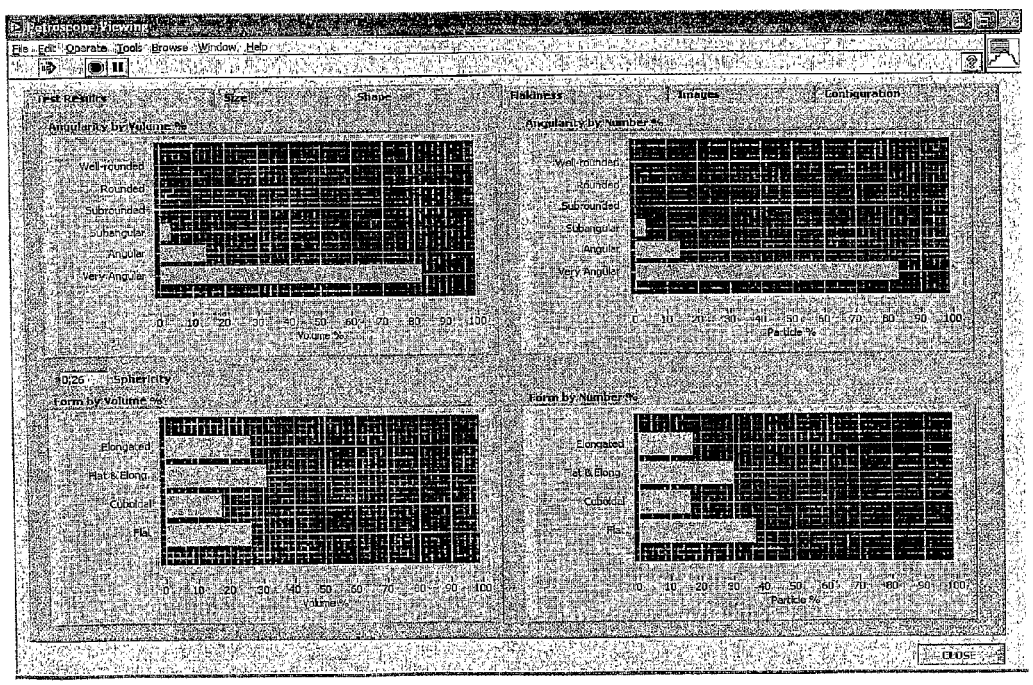

The term 'shape' as used herein generally refers to the macroscopic form and angularity of an object and preferably also the surface texture. As used herein the parameter 'form' is used to classify the analyzed objects according to the ratio of the main axes (long, intermediate and short axis) of the object. In accordance therewith, objects can be classified as shown in FIG. 9c in four classes, elongated, flat-elongated, flat and cuboidal. If all axes are substantially similar in length, the object is classified as cuboidal; if the intermediate and short axes are similar and the long axis substantially longer, the object is classified as elongated; if the long and intermediate axes are similar and substantially longer than the short axis the object is classified as flat; and if all the axes are different, i.e. the long axis substantially longer than the intermediate axis which is substantially longer than the short axis the object is classified as elongated-flat. Different cut-off values can be chosen to define the boundaries between the form classes, in one classification scheme two axes are considered similar if their ratio is less than 0.67 (shorter axis: longer axis), but this value can as well be set as e.g. 0.5 or 0.75.

These different forms can also be expressed in terms of a flakiness ratio or elongation ratio. Generally in the art, a particle is considered flaky if its thickness is less than 0.5 or 0.67 of its width and a particle is considered "elongated" if its width is less than 0.5 or 0.67 its length, depending on which standards are used. Such classification is readily accomplished with the methods of the present invention by grouping measured objects according to the measured main axis ratios and choosing appropriate intervals to define groups that will match classification according to comparative measurements with classical caliper measurements.

Figure 2A:
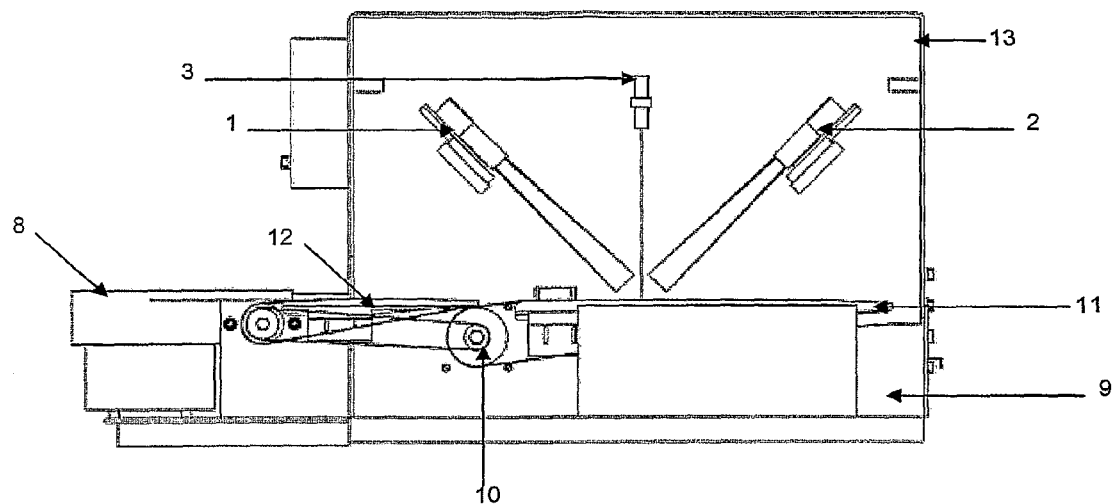
FIG. 2 shows an overview of a preferred apparatus of the invention.
Figure 2B:
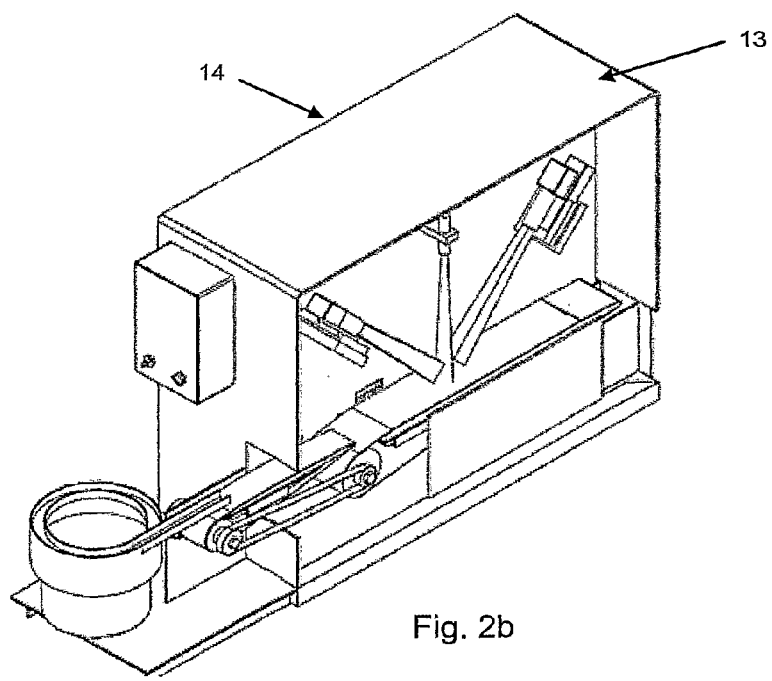

The apparatus comprises a feeder for feeding the sample objects onto a conveying belt such that the objects interspaced in a single layer stream not overlapping each other or in direct contact. In certain embodiments the objects are substantially aligned in a single line, such that one sample object at a time enters the detecting area of the apparatus, however, two or more objects may as well be detected simultaneously as long as the detection means and analysis software can differentiate between objects. A number of feeder solutions known to the person skilled in art can be employed in accordance with the invention, such as one or more conveyor belts arranged at an angle, e.g. perpendicular, with respect to the main conveying belt of the apparatus. The presently preferred embodiment comprises a vibrating spiral elevator 8 as shown in FIG. 2, the dimensions of which depend on the particular samples to be analysed. Suitable spiral elevators are provided by ScanVibro, Denmark. Other configurations may as well be used such as vibrating design feeders, which are provided e.g. by Vibratechniques Ltd, (UK).

The main conveyor 11 used in the apparatus can be readily selected by the skilled person and should preferably be driven with a suitable high precision motor to ensure a fixed speed of the conveyor during the operation of the apparatus. In one embodiment an electrical motor is used, the speed of which is directly dependent on the input AC frequency, the frequency is controlled precisely with an adjustable frequency controller. In the configuration shown in FIG. 2, a feeding conveyor 12 transmits the objects from the feeder 8 to the main conveyor 11, the feeding conveyor is set at a slower speed and aids in the discrete distribution of the objects. The main conveyor 11 is driven by a roller 10 axially connected to an electric motor fixed to the far side panel 14 of the cover 13. The open side of the cover 13 can as well be closed with a mountable front side panel (not shown).

Optical detection and Surface Analysis

The apparatus comprises an illumination source that casts a planar beam of light (i.e. collimated and preferably coherent light) across the main conveying belt, typically the beam is orthogonal to the direction of motion and preferably also to the plane of the belt. In one embodiment a coherent diode laser light is used with a suitable lens for creating a collimated planar coherent light beam. The width of the beam across the belt determines the maximum width of objects to be analysed, typically for conventional rock aggregate samples a beam width of about 40-160 mm is suitable, such as in the range of about 40-100 mm, e.g. in the range of about 40-80 mm, such as e.g. about 50 mm or about 60 mm, or wider such as about 100 mm, 120 mm, 140 mm or 160 mm. Longer objects can be analysed, provided that their long axis lies along the belt such that the width of the object across the belt is no more than the beam width. The width of the beam across the beam plane itself affects the resolution of the surface analysis, preferably the width at the maximum surface height of the object to be analysed is less than about 0.1 mm, such as 0.05 mm or less. It is however difficult to define the width of the beam; the observed width will depend on the ambient light level, the texture of the surface on to which the light is projected, etc. and in particular on the lens configuration which is suitably configured such that the beam is focused at the estimated particle height, e.g. 30-40 mm from the conveyor belt, or lower for samples of smaller particles.

The invention is particularly useful for the analysis of gravel size aggregates (from about 2-4 mm to 40-60 mm) and stone size aggregates from about 20-40 to about 160 mm) and may as well be used for sand size particles (about 0.5 to 2 mm) although different feeder configurations may be needed, such suitable solutions are known to the skilled person.

The image capturing means comprise at least one image detector, typically a machine vision camera with a lens and CCD or CMOS detector, the lens is selected with a suitable focal length. The detector(s) are arranged such they can capture an image of the diffuse reflection of the planar light beam illuminating an object conveyed through the beam path. The image detector is controlled to capture images with a short regular interval such as about 10 images per second or higher, such as about at least 20 images per second, including at least 24 or at least 26 images per second. With faster processors, a higher rate can be obtained such that in the range of about 25-120 images per second can be obtained, such as about 40 or 48 image per second, or up to 75 or 100 images per second. The image capturing frequency determines the allowed speed of the conveyor and thus the throughput of the measurement. For high-throughput analysis a high image capture frequency is desired, such as at least 50 images per second or at least 100 or 120 images per second. The software and control system of the present invention allows for high-throughput analysis and can with the presently systems configuration be configured such that at least about 100 objects of less than 100 mm widest diameter (long axis) are analysed per hour, and preferably at least about 200 rocks of less than 100 mm widest diameter per hour. Longer elongated objects can however be analyzed, provided the such elongated objects lie in parallel with the conveyor belt and the width of the object across the belt is less than the width of the beam. Consequently, the feeder of the apparatus is preferably configured such that objects are arranged on the conveyor with the longest axis along the direction of the belt.

Figure 1:
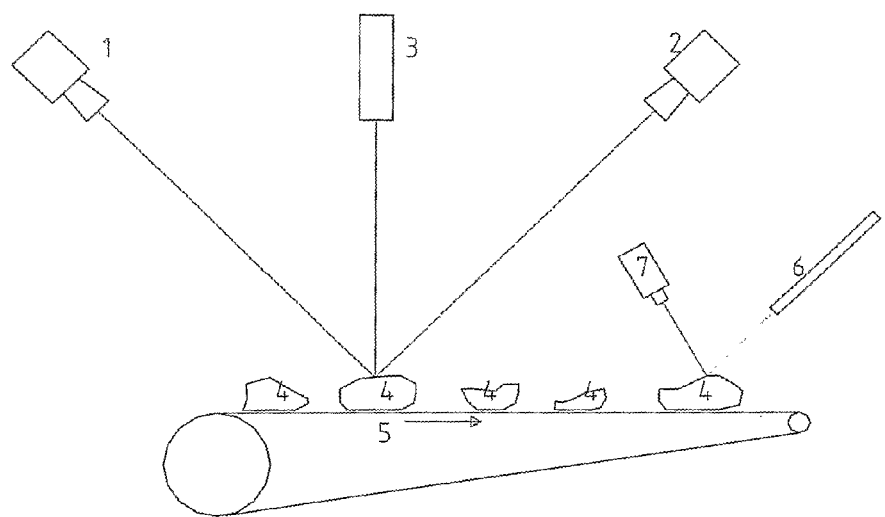
FIG. 1 illustrates schematically the general setup of the laser-camera triangulation system for optical detection and surface analysis. Two cameras 1 and 2 are shown and a laser 3 directing a laser beam towards an object 4. The arrow 5 shows the direction of the motion of the conveyor 11. 6 shows an optionally included source of IR/VIS light and 7 is an optional spectrophotometer for measuring the IR/VIS absorbance of the sample objects 4.

In a preferred embodiment at least two image detectors are used, preferably such that they are arranged to capture images of said reflection of the planar beam, the detectors being oriented to the object from a different angle to the planar beam, preferably one on each side of the planar beam and aligned such that each of the image planes have a horizontal axis perpendicular to the direction of the conveyor belt, in parallel with the planar beam. In other words, the detectors are preferably aligned with the direction of the belt, one in front of the beam and the other opposite the beam, as illustrated in FIG. 1 and FIG. 2.

The apparatus further comprises a control system being provided with processing means having stored therein a computer program and a memory, for controlling mechanical and hardware parts of the equipment and for storing captured images, the control system being adapted to process a sequence of images of said object to automatically determine the size and shape of said objects and returning parameters representing the size and shape, including angularity and form, of the objects and preferably also petrological composition of sample objects.

In one embodiment of the apparatus the control system is adapted to process the sequence of images and the resulting three-dimensional surface image of said object based on a computer program and calculating one or more of the following parameters: size of the objects; length of long, intermediate and short axis; elongation ratio and flakiness ratio; shape class; equivalent shape index; equivalent flakiness index; sphericity; roundness or angularity value and/or class; and statistical distribution of one or more of said parameters for a plurality of analyzed particles.

In a preferred embodiment the control system is adapted to process the sequence of images implementing a mathematical morphology algorithm to calculate a pseudo-volume loss value which is correlated to a roundness or angularity parameter and/or class.

The angularity of a rock particle is traditionally described using one of six categories on the Powers scale, where 1 is 'very angular', 2 is 'angular', 3 is 'sub-angular', 4 is 'sub-rounded', 5 is 'rounded' and 6 is 'well-rounded', as originally suggested by Powers. (Powers, M. C. "*A new roundness scale for sedimentary particles*" Journal of Sedimentary Petrology (1953) Vol. 23, pp. 117-119.)

As described in more detail herein, an angularity scale can be construed based on the angularity measurements according to the invention. The scale can be based on the '% volume of angles' determination where appropriate cut-off values can be selected to create intervals that classify the objects substantially as if classified by manual inspection according to the Powers scale. The inventors have found that it is possible to classify automatically with the apparatus and method of the invention particles in classes according to the Powers angularity definition with good statistical correlation to independent classification by manual inspection.

Morphology Analysis

Figure 3:
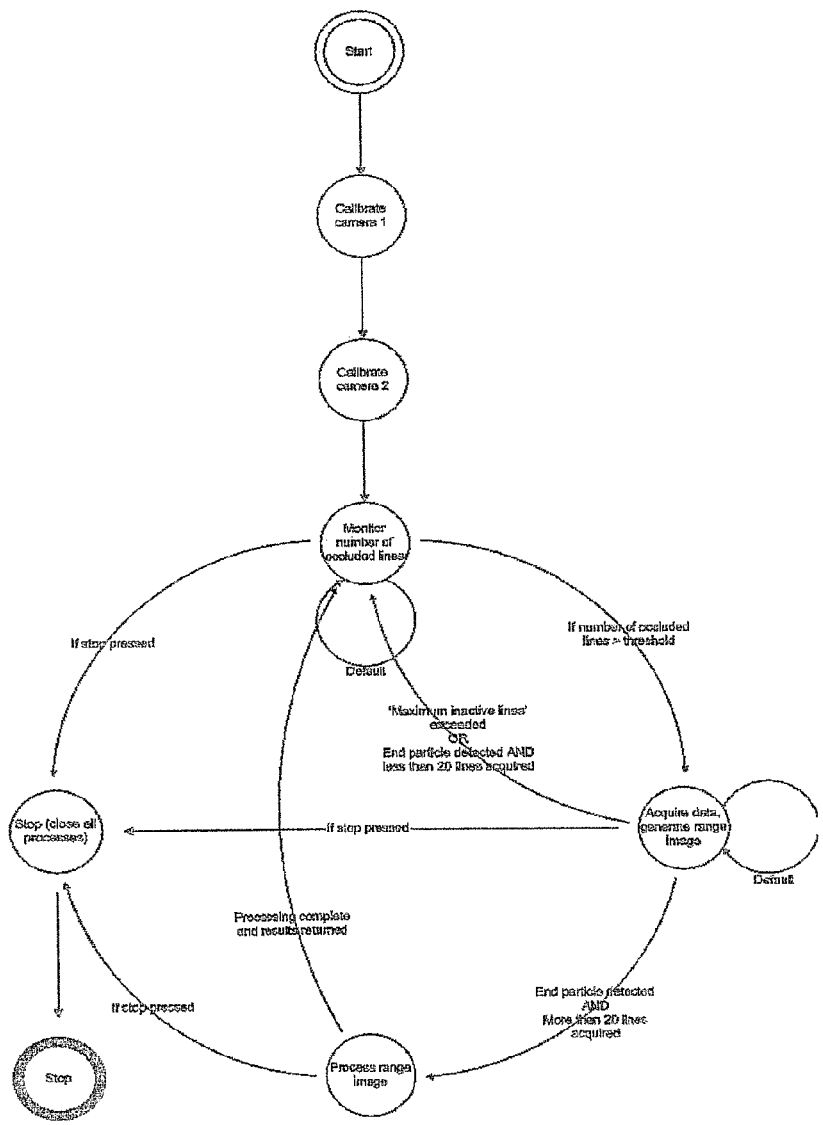
FIG. 3 is a schematic diagram of the program structure of a portion of the control system and program for the optical detection surface analysis, as described in more detail in Example 1.
Figure 4:
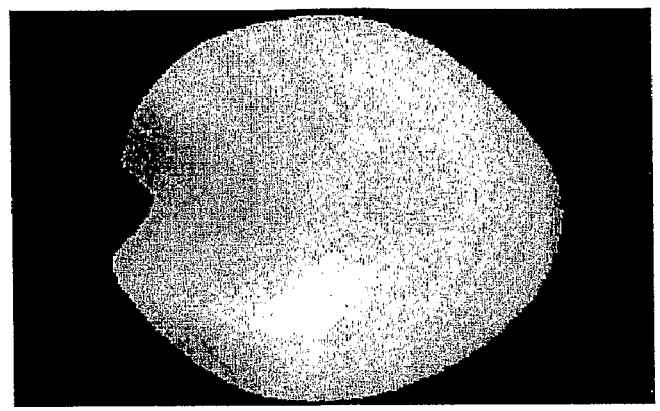
FIG. 4 shows a range intensity image free from occlusion and perspective effects, representing a particle to be analysed by the mathematical morphology algorithm described herein.

The dual camera laser triangulation system of the preferred embodiment of the invention allows sufficient surface coverage, effectively providing a complete model of the upper hemisphere of the particle. Each particle can thus be represented as a range image free from occlusion and perspective effects, as shown in FIG. 3.

There is a natural affinity between range imagery and greyscale morphology. The cloud data gathered using laser triangulation and represented in the range image is effectively a free surface in $\mathcal{R}^3$ space. In order to characterise the morphology of the particle we need to assume that the object is solid in the occluded region beneath the visible surface. A grey level image, denoted as a function $f(x,y)$ in $\mathcal{R}^2$ space, is considered in greyscale morphology to be a set of points [x, y, f(x, y)] in $\mathcal{R}^3$ space. The umbra $U[f]$ can be defined as:

$$U[f] = \{p(x,y,z) : z \leq f(x,y)\} \quad \text{(Eq. 1)}$$

The umbra of a set X in $\mathcal{R}^3$ space is thus the volume of points contained within the shadow of X, where the illuminant is a point light source at an infinite distance in the positive z-direction (Stanley R. Sternberg, S. R. Grayscale Morphology CVGIP 35 (1986), pp. 333-355). This corresponds to the direction of illumination in the laser triangulation system and the umbra is thus analogous to the shadow cast by the laser.

Greyscale erosion and dilation are then defined as follows. The erosion of an image f with a structuring element g involves translating the structuring element to every point on the image and taking a 'minimum of differences', thus:

$$(f \ominus g)(i, j) = \min\{f(i-x, j-y) - g(x, y) : (i-x, j-y), (x, y) \in Z^2\} \quad \text{(Eq. 2)}$$

Similarly, for a greyscale dilation we translate the structuring element to every point on the image and take a 'maximum of sums', thus:

$$(f \oplus g)(i, j) = \max\{f(i-x, j-y) + g(x, y) : (i-x, j-y), (x, y) \in Z^2\} \quad \text{(Eq. 3)}$$

In their standard form these operations are highly sensitive to noise and localised intensity variations. This is of particular concern when dealing with range imagery, as any impulse noise due to laser speckle and point occlusion could have a major impact on processing results. In soft morphology, the maximum and minimum operators used in dilation and erosion are replaced with more general weighted order statistics. The structuring element consists of a 'hard' centre and a 'soft' boundary, where the centre is weighted to wield more influence on the operation than the boundary. We thus define a structuring system [B,A,k] consisting of three parameters, finite sets A and B, $A \subset B$, and a natural number k satisfying $1 \leq k \leq |B|$. B is the structuring set, A its hard centre, k its order index or repetition parameter. We denote the $k^{th}$ smallest and $k^{th}$ largest member of a set by $\min^{(k)}$ and $\max^{(k)}$ respectively, and in keeping with the convention used by Koskinen et al (Koskinen et al. Soft Morphological Filters Proceedings of SPIE (1991) Vol. 1568, pp. 262-270), we use $\diamond$ to denote the repetition operation.

The soft erosion of an image f with a structuring system [B,A,k] is then best defined by:

$$f \ominus [B, A, k](x) = \min^{(k)}[\{k \diamond f(a) : a \in A_x\} \cup \{f(b) : b \in (B-A)_x\}] \quad \text{(Eq. 4)}$$

Similarly, the soft dilation of f by [B,A,k] is defined by:

$$f \oplus [B, A, k](x) = \max^{(k)}[\{k\langle\rangle f(a) : a \in A_x\} \cup \{f(b) : b \in (B-A)_x\}] \quad \text{(Eq. 5)}$$

The careful selection of an appropriate structuring element is critical to the efficacy of any morphological operation. In the analysis of objects in accordance with the present invention, the structuring element needs to be invariant to both the orientation of the particle and the inclination of the particle surface at any point. The morphological opening should also result in a minimum loss of volume in particles with a well-rounded surface. A suitably sized sphere is the ideal choice under these constraints. Again this is represented as a range image. When using this approach, actually a discrete approximation to a hemisphere is being used, rather than a genuine continuous sphere. The application of morphological openings or closings to greyscale images, using a structuring element with grey values representing the surface of a hemisphere, are generally known as rolling ball transforms, originally described by Sternberg (ibid.) as a means of smoothing discontinuities and removing noise in standard intensity images.

Figure 5A:
FIG. 5 illustrates how volume loss ("volume lost" or "volume of angles") of an angular surface is determined by a 'rolling ball' mathematical morphology approach; the original surface is shown in FIG. 5a, the transform is then applied (FIG. 5b) and any points that cannot be accessed by the ellipsoidal structuring element are deleted (FIG. 5c).
Figure 5B:
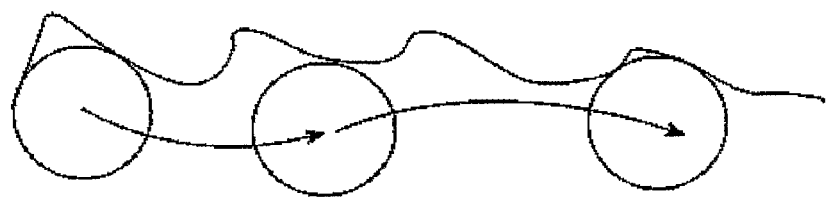
Figure 5C:

The approach can be described as follows. In the case of a morphological close, imagine rolling a ball over the three-dimensional surface described by the grey levels present in the image. If the surface is smooth with relatively low curvature, the ball will make contact with the surface at every point. However, the ball will not make contact with surface points contained within narrow pits or troughs, i.e. where the curvature of the concavity exceeds that of the sphere. The resultant function is then the union of every path that the ball may follow, or more specifically the union of the translations of the spherical structuring element to every point on the surface. Any narrow pits or troughs in the surface are thus 'closed'. Similarly, the morphological opening can be visualised as rolling a ball over the underside of the three-dimensional surface. In this case, it is protrusions of high curvature, such as sharp edges and corners, that are lost to the procedure. This is illustrated in FIG. 5. The original surface, shown as a cross-section, can be seen in FIG. 5*a*. The transform is then applied (FIG. 5*b*). Any points on the surface that cannot be accessed by the sphere are deleted (FIG. 5*c*).

On this basis we contend that the opening of a range image of a particle, using an appropriately sized spherical structuring element, can provide a means of discriminating between different classes of angularity simply by analysing the proportion of volume lost ('volume of angles') due to the procedure. This effectively simulates the natural wear process by which rock particles such as sand and gravel become rounded, by reducing each particle to a 'well-rounded' state. We would suggest that in this case the boundary of the structuring element should wield equal influence to the centre, so A=B with respect to equations (4) and (5). The rank parameter k can then be selected according to the anticipated level of noise in the range images.

The discriminatory ability of this approach will clearly depend to a large extent on the careful selection of the diameter of the spherical structuring element used. Indeed, the original methodologies proposed for manual petrological classification define angularity with respect to the size of the particle. The approach used by Wadell (Wadell, H. *Volume, shape and roundness of quartz particles*, Journal of Geology (1935) Vol. 43, pp. 250-280), generally considered as authoritative and from which the widely used Powers scale (Powers, ibid.) was derived, involves dividing the average radii of the corners of a two-dimensional grain image by the radius of the maximum inscribed circle. Given that a typical aggregate sample may contain particles of vastly different sizes, it seems intuitive that the size of the structuring element should be dynamically selected according to the size of the particle being analysed. However, further consideration leads us to question the use of a spherical structuring element. Firstly, the height of the particle, considered to be the dimension orthogonal to the image plane, will have no impact on the absolute volume loss. Particles with proportional larger heights stand to lose proportionally less volume. In addition to this, the angularity of a corner is traditionally measured with respect to a maximum inscribed circle in the given projection (Wadell, ibid.). However, a sphere of suitable proportions with respect to one projection may be inappropriate for another. Thus, in order to remove bias associated with the elongation and flatness ratios of the particle, we replace the spherical structuring element with an ellipsoid with aspect ratios identical to those of the particle undergoing analysis. The axes of the structuring element remain aligned with the axes of the particle at all times during the procedure, ensuring that proportionality is maintained from any arbitrary two-dimensional projection.

Figure 6A:
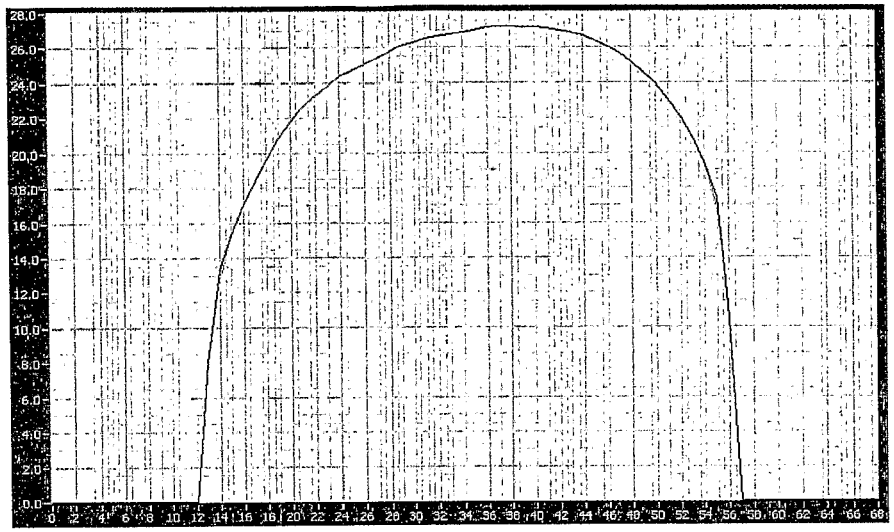
FIG. 6a represents a well-rounded particle, FIG. 6b a sub-rounded particle and FIG. 6c an angular particle.
Figure 6B:
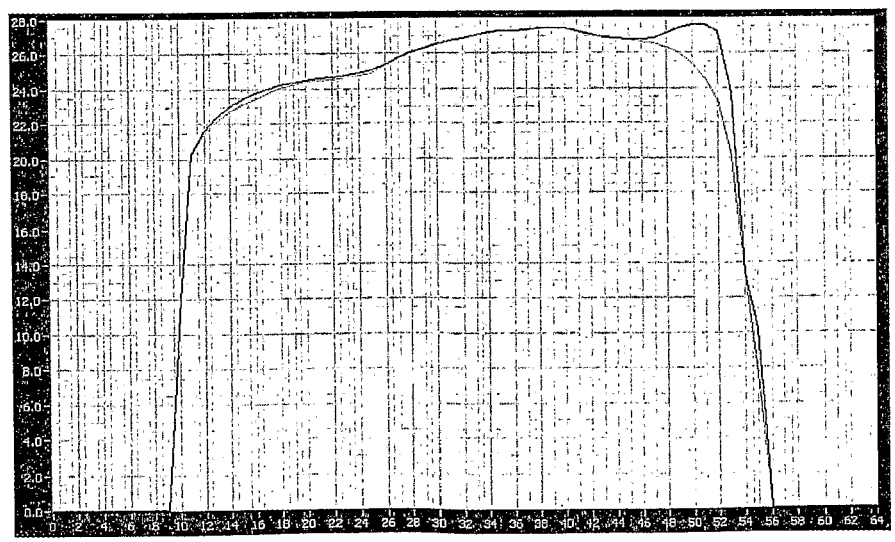
FIG. 6 shows cross-sections of three particles derived from captures range images. The outer line represents the original boundary and the inner line represents the boundary after the morphological opening.

As the dimensions of aggregate particles are seen as fundamental properties and are determined as a matter of course, it is straightforward to adaptively generate a structuring element of similar proportions. Empirically, the inventors have found that a structuring element with semi-axes ⅙ the length of those of the particle gives optimal results. It is as well contemplated that structuring elements with the same aspect ratio as the particle being analyzed but with another proportionality constant may as well be used, e.g. having semi-axes with a value in the range of about ⅓ to 1/10, such as he range of ¼ to 1/10 of the axes of the particle, such as about ¼, about ⅕, about ⅐ or about ⅛. FIG. 6 shows cross-sections of three particles derived from the captured range images. The outer line represents the original boundary and the inner line represents the boundary after the morphological opening. FIG. 6*a* was taken from a well-rounded particle. It can be seen that the boundary remains practically unchanged, volume loss is negligible.

Figure 6C:
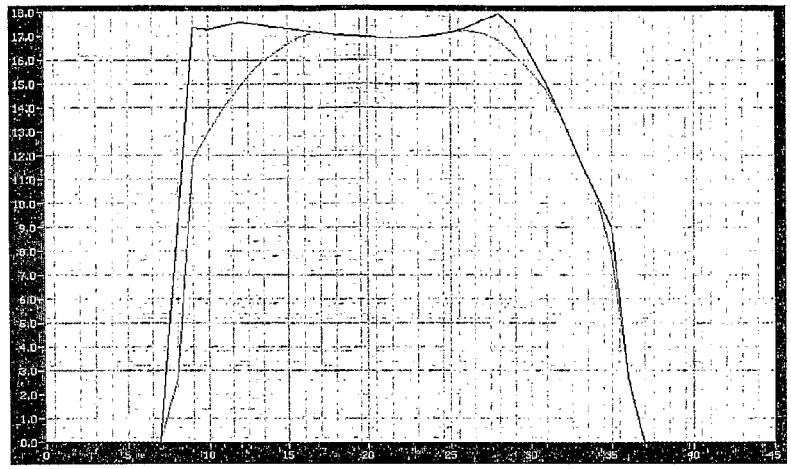

It should be noted that when viewing cross sections such as shown in FIG. 6, the volume loss does not necessarily correspond to the visible profile. For example, in FIG. 6*c*, volume loss down the left hand side of the profile corresponds to a corner not visible in this projection.

Texture Analysis

The images acquired as described above can as well be used to determine finer texture (roughness) of the particles and preferably also intermediate texture (porosity) as well. This is readily achieved by analysing at least a portion of the peripheries of a particle in an image or a profile across the upper hemisphere of the particle, where the roughness (undulance) of the peripheries will give an indication of the fine texture of the surface (smooth/rough).

Absorbance/Reflectance Measurement and Classification

A useful embodiment of the apparatus comprises a light source providing a beam of visible and/or infrared light and a spectrophotometric detector for detecting the reflections of said beam from an illuminated spot of said object and measuring visible and/or infrared absorbance or reflectance spectrum, the control system being adapted to process said spectrum and to compare it to reference spectra and/or spectral values based on reference materials to classify said object according to a predetermined class system of types and/or variants of mineral and rock particles and the like objects. Thereby, the apparatus and method of the invention are able to automatically classify rock samples, aggregates and the like in accordance with a pre-determined classification system.

The apparatus is preferably configured to classify samples according to the classification system as set out in European standard EN 932-3, such that sample objects representing at least 10 of the more common classes and preferably at least 15 or 20 of said classes can be determined automatically.

The classification system groups rock types as follows: Plutonic igneous rocks: granite, syenite, granodiorite, diorite, gabbro; hypabyssal igneous rocks: dolerite, diabase; extrusive igneous rocks (volcanics): rhyolite, trachyte, andesite, dacite, basalt; sedimentary rocks (divided into two groups based on their origin): clastic rocks: sandstone, conglomerate, breccia, arkose, greywacke, quartzite, shale (siltstone); non-clastic, chemical and biogenic rocks: limestone, chalk, dolomite, chert; metamorphic rocks: amphibolite, gneiss, granulite, hornfels, calcitic/dolomitic marble, quartzite, serpentine, schist, slate, mylonite.

Although, it is highly preferred that the apparatus and method of the invention are able to classify any given sample object in any one of the above classes, in some practical applications it will be highly useful to readily determine a number of main classes, each of which may comprise one or more of the above classes, samples of which have similar aggregate properties and thus do not need to be distinguished for industrial/construction use.

Two major routes are preferred for the spectral analysis and comparison to reference spectra and/values, either using statistical methods using statistical classifiers or using neural networks.

Neural networks consist of an interconnected net of their basic units, the so-called neurons. The neuron receives an information vector containing R different values and multiplies each value $p_i$ with a discrete weight, $w_i$. The sum of these products, i.e. the dot product of the p and w vectors, plus possibly a bias b, is the input into the neuron's transfer function $\theta$ which returns an output value a. The network is "trained" before real sample analysis can proceed, the product of this training is a collection of adjusted weights which can be expected to return a correct value, i.e. class number, when given input values for an unknown sample.

The inventors have found useful in the methods of the invention to apply statistical methods using a wavelet approach. Wavelets have adequate local properties and have turned out to be appropriate for statistical modelling of high dimensional data. In one embodiment, Daubechies wavelets with two vanishing moments are used. Classification accuracy can be improved by use of several measurements from different positions of each reference sample object. For such mean measurements, a reliable prediction of the class membership can readily be derived by use of wavelets.

The visible and infrared light source preferably provides visible and infrared light comprising the wavelength range from about 340 to about 4000 nm such as preferably from about 340 to about 1200 nm, wherein a suitable detector is selected that detects said range.

Suitable spectrophotometric detectors can be readily selected by the skilled person, e.g. such as the AvaSpec Spectrometers from Avantse (eerbeek, Netherlands) who also supply suitable light sources that can be selected to provide light in the suitable wavelength range.

It should be noted that the novel aspect of the invention pertaining to the spectroscopic analysis can be implemented as a stand-alone embodiment, i.e. an apparatus comprising the necessary above described features for spectroscopic analysis of objects and automatic petrographic analysis as described herein. Such an apparatus would generally comprise a suitable feeder and conveyor preferably as described for the above embodiments; a light source providing a beam of visible and/or infrared light and a spectrophotometric detector for detecting sequentially the reflections of said beam from an illuminated spot of said object and measuring visible and/or infrared absorbance or reflectance spectrum as described above, the apparatus having a control system for a spectral analysis and comparison with reference spectra/values as described in further detail herein.

The invention provides in another aspect as mentioned above, a computer program product for carrying out data analysis and preferably also for controlling data acquisition in methods as described herein, for automatic analysis of image data as describe herein for automatic analysis of sample objects as defined above. The computer program product comprises instruction means to instruct a computer processor when loaded and run on a computer to receive input data from at least two image detectors configured to capture at a minimum pre-determined frequency sequential images of the reflection of a planar coherent beam shining across the direction of a stream of said objects moving at a pre-determined rate, store said images and process images for each object to obtain data indicating the size of said object and three-dimensional surface data or a contour map and topographical data representing said object, determine based on said obtained data one or more size parameters and shape parameters for said objects, where said shape parameters comprise a form parameter and/or classification indicating whether particles are elongated and/or flat and an angularity/roundness parameter and/or classification.

The computer program product preferably utilises any or all of the above described analysis methods and morphological algorithms.

In certain embodiments, the computer program product can be separated into substantially separate units, one unit for data acquisition and control of the measurement apparatus (calibration of conveyor speed, detectors, etc.) and another unit which may be run on a separate computer for data analysis and data presentation.

In a useful embodiment the computer program product is further adapted to input visible and/or IR spectral data obtained for each object as described above and analyse in accordance with the methods described herein in order to determine petrological or other compositional information as described above for the objects. Preferably said information comprises a classification of said object according to a pre-determined class system of petrological rock types and/or variants as described in further detail above.

The present invention is in no way restricted to the specific disclosure of the specification and figures, but also encompasses any modifications within the scope of the appended claims. For example, one could use or have different wavelengths of light from the ones specified here for the spectroscopic measurements and different lens and reflection probes; an extra camera for obtaining additional information on surface textural properties and colour; system for sorting the objects after the measurement and according to results of the measurements; different type of feeder and system for controlling the input and output of particles or objects to and from the conveyor; more than one row of objects aligned for measurement. Also, the invented equipment could be used for measurement of size, shape or composition of other materials, like: Ores; drilled core specimens or crushings; otolith in fish; recycled building material; industrial minerals; decorative stone; chippings; metallic minerals and alloys.

EXAMPLES

Example 1

Guide to Program for Part of Size, Form and Angularity Analysis

The program structure is shown diagrammatically in FIG. 2. The following section briefly describes the role and functionality of sections of an initial version of a software embodiment.

Calibration of camera 1. A single frame is captured. For each column in the image, the brightest pixel (theoretically corresponding to the centre of the laser line) is located. When the pixel intensity exceeds 'min intensity' (used to distinguish between pixels attributable to the laser line and pixels corresponding to background light levels), 'Triangulation algorithm subVI' is called to calculate height at that point. A 1D array of height values is thus generated for the frame. The median value is taken to be the height of the belt. This is used as a reference value in all subsequent triangulation calculations.

The median value is taken because the majority of the columns in the image frame should be covered by the laser line. Thus selecting the median means that we don't pick a height value corresponding to an occluded line. Furthermore, we also exclude outliers caused by dust etc.

Calibration of camera 2, same procedure as described above for camera 1.

"State Machine"

State 0: Responds to a 'stop' command. Closes images, clears memory, etc.

State 1 (initial state): Continuously acquires frames from camera 1 (parallel with the direction of motion). Calls 'Occlusion-based particle detector subVI' to count the number of occluded lines in each frame. If the number of occluded lines exceeds 'occlusion trigger level'—indicating that an oncoming particle is occluding the laser line from the camera, the system moves into state 2. If stop is pressed at any time, the system moves into state 0.

State 2 (acquire data): Continuously acquires frames from both cameras. Calls 'Calibrated triangulation subVI' to generate arrays of height data. Calls 'Merge lines subVI' to merge the height data generated from each camera.

The routine uses a Boolean latch to indicate when the system has started acquiring data from the surface of the rock (i.e. when the height values returned by 'Calibrated triangulation subVI' exceed the minimum height threshold. This is initially set to false, and latches to true as soon as a positive height value is returned.

Stopping criteria 1: If the latch remains false for more than a predetermined number of lines ('maximum inactive lines' control), there is clearly not a particle under the laser and the trigger must have been false. In this case, the routine will stop acquiring data and return to state 1.

Stopping criteria 2: If the latch has been triggered (i.e. set to true) and neither camera is acquiring any positive height data, this should indicate the end of a particle. However, as this could be caused by occlusion mid-particle it is necessary to allow a certain tolerance. As such, every time a pair of frames is captured and these conditions are met, a counter is incremented. If either camera subsequently acquires positive height data, the counter is reset to zero. If the counter exceeds a predetermined value ('Grace count'), the system stops acquiring and proceeds to state 3.

Stopping criteria 3: If the stop button is pressed at any time, the system switches directly to state 0.

Stopping criteria 4: If an acquisition error occurs at any time, the system stops acquiring and prompts the user.

If less than 'minimum acquired lines' (user control) are acquired in this state, the system will switch back to state 1 instead of state 3. This indicates a particle too small to be processed.

State 3 (process the range image): This state takes the merged range image in array format as an input and calls all the subVIs (subroutines referred to as sub-'virtual instruments' (cf. Labview software environment from National Instruments) necessary to quantify the properties of the particle. There is also an option for the user to select and view any arbitrary height profile across the particle, which is likely to be useful when setting up the device and running diagnostics.

Guide to subVIs

Occlusion-based particle detector subVI: This VI is used to detect the presence of rocks approaching the laser line. This works by monitoring the image (in array format) of the laser line seen by the camera facing the direction of motion. For each column in the image, the brightest pixel is located. If the intensity of the brightest pixel in a particular column is less than 'min intensity' (a user-determined threshold), that column is said to be occluded. For each frame captured by the camera, this VI thus returns the number of occluded columns.

Triangulation algorithm subVI: This software portion implements an algorithm that calculates the spatial coordinates of a single image point. The inputs are f (focal length of the camera lens in mm), d (distance between the centre of the lens and the conveyor belt measured along the camera axis in mm), theta (the triangulation angle in degrees), j (pixel coordinate in the vertical direction, measured by default from the top left of the image), i (pixel coordinate in the horizontal direction, measured by default from the top left of the image) and the camera sensor parameters (physical dimensions in mm and in pixels). The VI returns the y and z coordinate of the point, the x coordinate being determined by the position of the conveyor belt.

Calibrated triangulation subVI: This takes a single image frame (in array format) and locates the centre of the laser line in each column using a 'centre of gravity' technique. This VI then calls 'Triangulation algorithm subVI' for each located peak value and returns a line of height data.

Merge lines subVI: This takes the two lines of height data generated by 'Calibrated triangulation subVI' for each of the two cameras and merges them to produce a single line of height data. Prior to the execution of this VI, one of the lines must be reversed (the two cameras point in opposite directions) and the lines must be aligned so that particular elements of each linear array correspond to the same spatial location. The two lines are then merged on a point by point basis by the following criteria:

Does the height value returned by each camera differ by more than 'max difference?

If NO: Take the average of the two values

If YES: Do either of the values=0?

If YES: The point is occluded from one of the cameras. Take the largest of the two values as the height at that point.

If NO: The difference is probably due to a specular highlight or interreflection, which generally results in an artificially high spurious value. Take the smallest of the two values as the height at that point.

Any pixels with a height value of less than or equal to 10 are then set to 0, corresponding to the reference height level of the belt.

Width check subVI: This is used to aid the alignment and calibration of the two cameras. The input is a line of height data generated by 'Calibrated triangulation subVI'. The VI returns the width of the particle in pixels and the index of the furthermost left position of the particle. This VI can be used on the line returned by both cameras in order to eliminate the differences.

MM occlusion removal close subVI: This VI uses a grey level morphological close to eliminate any discontinuities (holes) within the boundary of the particle caused by a point being occluded from both cameras. The structuring element is designed to have a minimal impact on genuine surface features.

MM spike removal open subVI: This VI uses a grey level morphological open to eliminate any spikes (impulse noise) on the recovered surface caused by interreflections from concavities. The structuring element is designed to have a minimal impact on genuine surface features.

MinBoundingBox auto subVI: This VI determines the length and width of the particle. The acquired range image is thresholded (reduced to a binary representation, where one value represents the particle and the other represents the background). The orientation of the particle is determined using a standard IMAQ vision function, based around analysis of moments. The image of the particle is then rotated to align its principal axes with the coordinate system of the image. A minimum enclosing rectangle is fitted to the image. The longer side of the rectangle is taken to be the length of the particle and the shorter side is taken to be the width.

Calculate sieve size subVI: This VI calculates the minimum passable sieve size of a particle from its calculated width and height using a calculus approach. The volume of the particle as an equivalent ellipsoid is also calculated.

Collate form results subVI: This VI takes the numerical values for length, width and height and converts them into a format suitable for display.

Image resample subVI: This reduces the resolution of the image array by a specified reduction factor, prior to the determination of particle angularity.

RollingBall controller subVI: This VI provides a framework in which the operations necessary to calculate angularity can be undertaken. This VI calls 'Adaptive ellipsoid calculator subVI' to generate an ellipsoidal structuring element according to the dimensions of the particle under analysis. 'Rolling ball algorithm subVI' is then called to perform the morphological opening. The volume loss incurred by the particle is then converted into a Powers scale value.

Adaptive ellipsoid calculator subVI: Generates a hemi-ellipsoidal structuring element with principal axes $\frac{1}{6}^{th}$ those of the particle (after re-sampling).

Rolling ball algorithm subVI: Performs a morphological opening on a given image array using a given structuring element.

Sieve size distributions subVI: Updates the cumulative particle size distribution (represented as a discrete array with 0.5 mm increments) every time a particle is processed.

Example 2

Angularity Analysis of Rock Particles

A total of 200 rock particles in the 8-32 mm size range were scanned using the laser triangulation system and analysed by the ellipsoidal morphology algorithm. Prior to the analysis, the particles were visually assessed and graded manually according to the Powers scale by geologists at two independent institutions.

FIG. 6 shows a scatter plot of the pseudo-volume lost due to the morphological opening against the visually (manually) assessed angularity for each particle, represented in accordance with the Powers scale as a number between 1 (very angular) and 6 (well rounded).

Figure 7A:
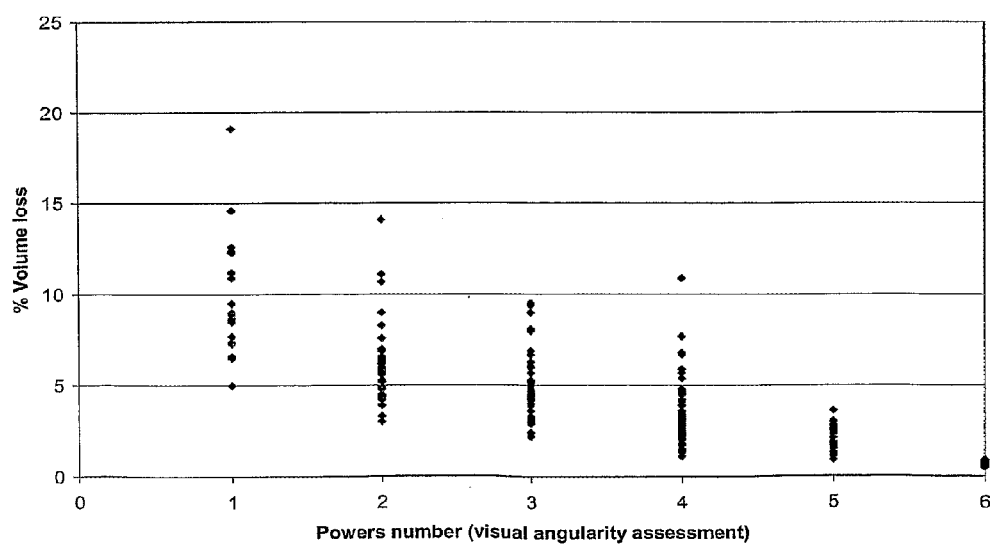
FIG. 7a shows a scatter plot of the volume loss as determined according to the invention (see Example 2) against the visually assessed angularity for each particle, classified according to the Powers scale, illustrating the variability of the volume loss within the higher angularity classes. 7b is a plot of the standard deviation of the percentage volume lost under each class against the Powers number assessed manually.
Figure 7B:
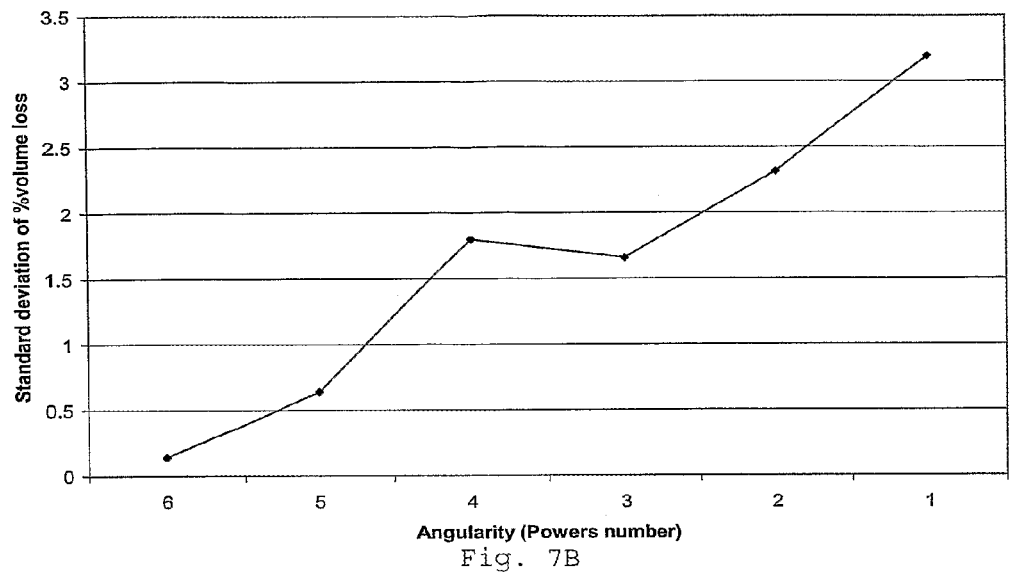
Figure 8:
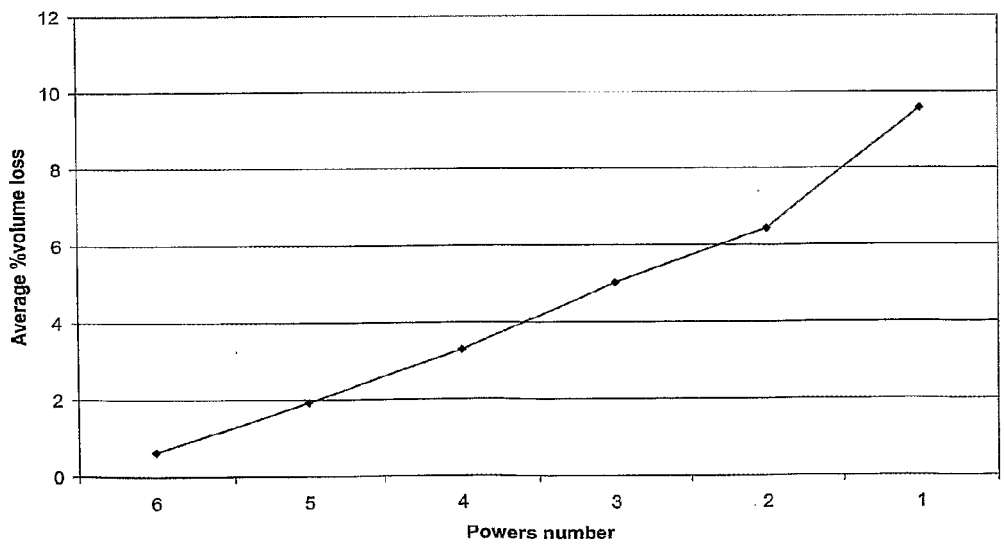
FIG. 8 shows the relationship between the average percentage volume loss determined automatically by the method of the invention and the Powers number for each category.

The first observation is that the deviation in the results is very large and appears to increase with angularity. This can be confirmed by plotting the standard deviation of the percentage volume lost under each category against the Powers number, as shown in FIG. 7*b*. It can be seen that the standard deviation increases at a fairly uniform rate as angularity increases as also indicated in FIG. 7*a* that shows the distribution of measure volume lost within each class. This suggests that the deviations are due to the difficulties in manually and objectively classifying angularity—a well rounded particle can easily be identified as such, whereas discriminating between more angular particles is much more difficult. In order to examine the effectiveness of the algorithm of the invention, the relationship is determined between the average percentage volume loss and the Powers number for each category. This is shown in FIG. 8. The correlation is clear, there is an almost linear relationship between the average percentage volume loss and the manually assessed Powers number. The results give a correlation value of 0.987.

Example 3

Petrographic Analysis

A method was developed to obtain information about the texture of analysed rock samples. The texture is mostly influenced by the sizes of individual crystals and therefore gives information that can be important for classification, as the crystal-size of rocks can vary depending on their type.

In short the method works as follows: It starts by locating the sample in a two-dimensional image taken by a digital camera (e.g. CCD or CMOS type industrial camera) located above the object (e.g. after the laser light and camera assembly used for the angularity assessment) and selecting a part from its middle, in order to evade background and shadows. The picture is then converted into a grayscale image and the number of graytones reduced to between 2 and 25. Experiments were made with different numbers of colors and this interval, 2-25, seemed to give good results, and seemingly the best results were in the interval 4-8.

After the reduction of colors, each pixel is evaluated and a so-called co-occurrence matrix is created which contains information about the likelihood of two neighbouring pixels being of the same color. Intuitively it can be seen that if the rock has big crystals it is more likely that neighbouring pixels have the same color, and vice versa.

In the co-occurrence matrix, P, each entry $p_{ij}$ represents the number of cases in which a pixel of grayscale value i is in the predefined distance d from a pixel of value j, with d normally being a vector pointing to the next pixel to the right, or possibly a collection of vectors so that all surrounding pixels may be evaluated. The diagonal entries of P, that is all entries $p_{ij}$ where i=j, represent the number of cases in which the compared pixels have the same color. Therefore, in samples with big crystals, the biggest values within P are situated on the diagonals or close to them, while for samples with small crystals the values are more evenly distributed about the matrix.

After the co-occurrence matrix P had been constructed the following equations were used to derive information about the texture, more or less by evaluating the distribution of the values within P:

$$\text{Energy} = \sum_i \sum_j P^2(i, j) \quad \text{(Eq. 5)}$$

$$\text{Entropy} = -\sum_i \sum_j P(i, j) \log P(i, j) \quad \text{(Eq. 6)}$$

$$\text{Contrast} = \sum_i \sum_j (i-j)^2 P(i, j) \quad \text{(Eq. 7)}$$

$$\text{Homogeneity} = \sum_i \sum_j \frac{P(i, j)}{1 + |i-j|} \quad \text{(Eq. 8)}$$

The samples analysed in the Example were additionally spectroscopically measured in addition to being photographed as described above. The samples were of four different rock types, two of which were divided into two variations. The four rock types were basalt, gabbro, rhyolite and granite. Both the basalt and granite samples were further divided into two categories or varieties. Hence, the samples represented six different rock samples, and each contained ten sub-samples, see table 1. The samples were measured in two different fields of the spectrum: in the region or range 400 to 1100 nm, here referred to as the Visible Range (VIS), and in the range 1000 to 3000 nm, here referred to as the Near-Infrared Range (NIR) and finally in the Mid-Infrared Range (MIR), 3000 to 30000 nm. Each sub-sample was measured in one spot in VIS and three spots in MIR and NIR. Altogether 60 measurements were obtained in VIS and 180 in MIR and NIR respectively.

Results

Visible Region (VIS)

Although the spectrum of the samples is rather homogeneous in the visible region (here 400-1100 nm), with a rather constant slope and few "valleys" and "hills", its classification was quite accurate. Bearing in mind the limiting number of measurements, that is 60, an accuracy of approximately 80 percent is probably more than one would have expected. Also, by doing more measurements it should be easy to improve the classification. A common factor in the classification in all of the spectrums, i.e. VIS, NIR and MIR, was that the error most frequently occurring was when classifying samples of class or number 4 and 5. In those cases, samples of class 4 were almost without an exception classified as belonging to class 5, and vice versa. In view of this and the fact that samples of class 4 and 5 would in most cases be regarded as a similar type of aggregate (being of the same rock type), a classification was made where those two classes were taken as one. That increased the classification accuracy dramatically, going up to as much as 98 percent although a more realistic accuracy would probably be between 90 and 95 percent.

Near-Infrared Region (NIR)

The spectrum in the near-infrared region is quite homogeneous but has more apparent features that one can use to distinguish between classes by looking at their spectrum. In short, a classification accuracy as high as 95 to 98 percent could quite easily be obtained, the only errors occurring in classes 4 and 5. After reducing those to one class, the accuracy was without an exception 100 percent.

Example 4

Automatic Analysis and Data Presentation

A user-friendly program and computer interface has been developed for presentation of data gathered from high-throughput analysis of rock particles with an apparatus as shown in FIG. 2. Screen views showing examples of the output from the computer program are shown in FIG. 9.

(i) Size Determination

The program determines the main axes of each object from the acquired image, where the long axis (L) is the longest distance between two points of the object, the intermediate axis (I) is the longest axis orthogonal to the main axis and the short axis (S) is orthogonal to the other two axes.

The size of each particle is indicated with a volume parameter, i.e. the calculated volume of an ellipsoid with outer dimensions corresponding to the main axes. This determination will thus substantially correspond to a size measurement as defined in European standard No. EN 933-1.

(ii) Form Classification

Based on the ratio between the axes each object is classified in one of four groups: elongated, flat and elongated, flat and cuboidal.

TABLE 1

Samples

| Sample no. or class | Rock type | Variety | | | Stage of porosity | | | Place name | No. of sub-samples | No. of spots measured in each sub-sample | | |
|---|---|---|---|---|---|---|---|---|---|---|---|---|
| | | Stage of alteration | | | DP (dense or slightly p.) | MP (medium p.) | HP (highly p.) | | | VIS | NIR | MIR |
| | | FA (fresh or slightly a.) | MA (medium a.) | HA (highly a.) | | | | | | | | |
| PM-001 | Basalt | x | | | x | | | Seljadalur | 10 | 1 | 3 | 3 |
| PM-002 | Basalt | | x | | x | | | Glerá | 10 | 1 | 3 | 3 |
| PM-003 | Rhyolite | | | | x | | | Glerá | 10 | 1 | 3 | 3 |
| PM-004 | Granite | | I: Migmatite granite (gneiss) | | | | | Hiskula | 10 | 1 | 3 | 3 |
| PM-005 | Granite | | II | | | | | Hiskula | 10 | 1 | 3 | 3 |
| PM-006 | Gabbro | | | | | | | Rappukallio | 10 | 1 | 3 | 3 |

If both ratios S/I ("flakiness ratio") and I/L ("elongation ratio") are larger than 0.67 the object is cuboidal; if I/L≧0.67 and S/I<0.67 the object is flat; if I/L<0.67 and S/I≧0.67 the object is elongated; and if I/L<0.67 and S/I<0.67 the object is elongated-flat. Note that other cut-off values may as well be used, e.g. 0.5.

Each object is classified in the appropriate class and an accumulated distribution of particles in the different classes calculated both based on number of particles and the total accumulated volume of particles.

The obtained determination can be directly correlated with the shape index and flakiness index as defined by European standards No. EN 933:4 and No. EN 933:3, respectively, i.e. the obtained data give equivalent information as the calliper and bar sieve measurements described by these standards.

(iii) Angularity Classification

Angularity ("% volume of angles") is calculated for each particle based on morphological analysis of the acquired 3D image as described above. Each particle is classified in an appropriate class from a set of six classes (1) well-rounded, (2) rounded, (3) sub-rounded, (4) sub-angular, (5) angular, and (6) very angular.

The classification is linearly correlated to the calculated '% volume of angles'. The accumulated distribution of particles in the different classes is calculated both based on number of particles and the total accumulated volume of particles

The invention claimed is:

1. An apparatus for automatic analysis of size and shape of a plurality of sample objects selected from minerals, rocks, gravel, natural, manufactured or recycled aggregates and the like, the apparatus comprising:
   a) a feeder unit for feeding said objects interspaced in a stream onto a conveying belt;
   b) an illumination source that casts a collimated beam of light across said conveying belt;
   c) image capturing means comprising at least one image detector for capturing an image of the reflection of said planar beam illuminating said object;
   the apparatus further comprising a control system being provided with processing means having stored therein a computer program and a memory for controlling mechanical and hardware parts of the equipment and for storing captured images, the control system being adapted to process a sequence of images of said object to automatically determine the size, and shape of said objects by implementing a morphological algorithm to calculate a pseudo-volume loss value which is correlated to roundness or angularity parameter and/or the class, and returning parameters representing the size and shape of the objects, said shape parameters including parameters indicating form and angularity.

2. The apparatus of claim 1 wherein said image capturing means comprise at least two image detectors arranged to capture images of said reflection of the planar beam being oriented to the object from a different angle to the planar beam.

3. The apparatus of claim 1 wherein said feeder is selected from a vibrating spiral elevator or a dosing feeder.

4. The apparatus of claim 2 wherein said at least two image detectors are arranged one on each side of said planar beam aligned such that each of the image planes have a horizontal axis perpendicular to the direction of the conveyor belt, in parallel with the planar beam.

5. The apparatus of claim 1 configured to automatically analyze at least about 100 of said sample objects of less than 100 mm widest diameter per hour, and preferably at least about 400 of said sample objects of less than 100 mm widest diameter per hour.

6. The apparatus of claim 1 wherein the control system is adapted to process the sequence of images and the resulting three-dimensional surface image of said object based on a computer program and to calculating one or more of the following parameters: size of the objects; length of long, intermediate and short axis; elongation ratio and flakiness ratio; form class; equivalent shape index; equivalent flakiness index; sphericity; roundness or angularity value; and statistical distribution of one or more of said parameters for a plurality of analyzed particles.

7. The apparatus of claim 6, wherein the control system is adapted to determine a size parameter for said objects and a size distribution, a form class and form class distribution and an angularity class and angularity distribution.

8. The apparatus of any of claim 1 wherein said shape parameters further comprise a surface texture parameter indicating smoothness/roughness.

9. The apparatus of claim 1 wherein said morphological algorithm is based on the use of a structural elipsoidal element which element is defined for each particle being analysed having substantially the same aspect ratios as said particle.

10. The apparatus of claim 9, wherein the proportionality constant defining the ratio between the size of said particle and the size of said structural element is in the range of about 1:3 to 1:10 and preferably in the range of about 1:4 to about 1:10.

11. The apparatus of claim 1 further comprising a light source providing a beam of visible and/or infrared light and a spectrophotometric detector for detecting reflections of said beam from an illuminated spot of said object and measuring visible and/or infrared absorbance or reflectance spectrum, the control system being adapted to process said spectrum and to compare it to reference spectra and/or spectral values based on reference materials to classify said object according to a predetermined class system of types and/or variants of mineral and rock particles and the like objects.

12. The apparatus of claim 11 wherein the visible and infrared light source provides visible and infrared light comprising the wavelength range from about 340 to about 1200 nm, said range being detected by the detector.

13. The apparatus of any of claim 1 further comprising weighing means to weigh each object.

14. A method for determining size and shape of objects in a plurality of objects in a sample selected from minerals, rocks, gravel, natural, manufactured or recycled aggregates and the like, where the shape determination includes at least the determination of a form parameter or class indicating whether particles are elongated and/or flat and an angularity determination, the method comprising:
   feeding said objects interspaced onto a moving conveyor belt;
   illuminating the sequential stream of objects with a collimated beam of light across the direction of the conveyor;
   capturing images with at least one image detector, of the diffuse reflection of said planar beam illuminating said object and storing said images in a memory such that for each object a series of images is acquired and stored with a regular minimum frequency based on the pre-determined speed of the conveyor;
   processing for each object passed under the planar beam of light the series of images for said object to obtain three-dimensional surface data or a contour map and topographical data representing said object, which includes an ellipsoidal structuring element with axes proportional to those of the object used in a mathematical morphological algorithm to determine the angularity of the object;

determining based on said obtained data a size parameter and shape parameters for said objects, where said shape parameters comprise a form parameter and/or classification indicating whether particles are elongated and/or flat and an angularity parameter and/or classification.

15. The method of claim 14, comprising capturing images with at least two image detectors, one on each side of said collimated beam of light.

16. The method of claim 14 comprising compiling size and shape data, including form data indicating elongation and flatness and angularity/roundness data for each object in said plurality of objects and calculating parameters representing size and shape mean and variation values of the analyzed objects in said sample.

17. The method of claim 16 wherein the size of an object is represented by an ellipse calculated from the short and intermediate axis of the said object.

18. The method of claim 16, wherein size of objects is indicated by calculated volume based on measured dimensions and pre-determined shape.

19. The method of claim 18 wherein an ellipsoid is calculated from three axes that represent the outer dimensions of the object, wherein said ellipsoid provides an approximation of the volume of the object to generate a size distribution for a plurality of objects analyzed.

20. The method of any of claim 14, wherein said form parameter and/or classification comprises a form classification in to at least four classes indicating whether objects are substantially spherical, substantially flat, substantially elongated or substantially elongated and flat.

21. The method of claim 14 wherein the proportionality constant defining the ratio between the size of said particle and the size of said structural element is in the range of about 1:3 to 1:10 and preferably in the range of about 1:4 to about 1:10.

22. The method of claim 21 wherein said proportionality constant is in the range of about 1:4 to about 1:8.

23. The method of any of claim 14 wherein said angularity parameter and/or classification comprises a classification scheme with a plurality of classes.

24. The method of any of claim 14 further comprising illuminating each object fed to the conveyor with a visible and/or infrared radiation beam, detecting the reflection of said beam from the illuminated spot of said object and measuring the visible and/or infrared absorbance or reflectance spectrum, comparing said spectrum to reference spectral values to determine petrological or other compositional information for said object.

25. The method of claim 24 wherein said petrological information comprises a classification of said object according to a predetermined class system of petrological rock types and/or variants.

26. A computer program product loadable on a computer, for controlling acquisition of and analysing image data of a plurality of objects selected from minerals, rocks, gravel, natural, manufactured or recycled aggregates and the like, said computer program product comprising program instruction means to instruct a computer processor when loaded and run on a computer to:

receive non-transitory input data from at least one image detector configured to capture at a minimum pre-determined frequency sequential images of the reflection of a planar coherent beam shining across the direction of a stream of said objects moving at a predetermined rate;

store said images and process images for each object to obtain data indicating the size of said object and three-dimensional surface data or a contour map and topographical data representing said object, which includes an ellipsoidal structuring element with axes proportional to those of the object being analyzed is used in a mathematical morphology algorithm to determine the angularity of the object;

determine based on said obtained data one or more size parameters and shape parameters for said objects, where said shape parameters comprise a form parameter and/or classification indicating whether particles are elongated and/or flat and an angularity/roundness parameter and/or classification.

27. The computer program product of claim 26 further comprising program instruction means to compile size and shape data, including form data indicating elongation and flatness and angularity/roundness data for each object in said plurality of objects and calculating parameters representing size and shape mean and variation values of said plurality of objects.

28. The computer program product of claim 26 wherein said form parameter and/or classification comprises a form classification in to at least four classes indicating whether objects are substantially spherical, substantially flat, substantially elongated or substantially elongated and flat.

29. The computer program product of any of claim 26 wherein size of objects is indicated by calculated volume based on measured dimensions and predetermined shape.

30. The computer program product of claim 29 wherein an ellipsoid is calculated from three axes that represent the outer dimensions of the object, wherein said ellipsoid provides an approximation of the volume of the object to generate a size distribution for a plurality of objects analyzed.

31. The computer program product of claim 26 wherein the proportionality constant defining the ratio between the size of said particle and the size of said structural element is in the range of about 1:3 to 1:10 and preferably in the range of about 1:4 to about 1:10.

32. The computer program product of claim 31 wherein said proportionality constant is in the range of about 1:4 to about 1:8.

33. The computer program product of any of claim 26 further adapted to receive spectrophotometry input data from a spectrometer configured to detect reflections of a visible and/or infrared beam illuminating said object, and compare said data to reference spectral values to determine petrological or other compositional information for said object.

34. The computer program product of claim 26, wherein said petrological information comprises a classification of said object according to a predetermined class system of petrological rock types and/or variants.

* * * * *